United States Patent
Butler et al.

[11] Patent Number: 6,122,341
[45] Date of Patent: Sep. 19, 2000

[54] SYSTEM FOR DETERMINING TARGET POSITIONS IN THE BODY OBSERVED IN CT IMAGE DATA

[76] Inventors: William E. Butler, No. 4- 134 Prince St., Boston, Mass. 02113; Paul H. Chapman, 97 Chestnut St., North Reading, Mass. 01864; Eric R. Cosman, 872 Concord Ave., Belmont, Mass. 02178

[21] Appl. No.: 08/969,078

[22] Filed: Nov. 12, 1997

Related U.S. Application Data

[63] Continuation of application No. 08/711,348, Sep. 5, 1996, abandoned, which is a continuation of application No. 08/434,246, May 3, 1995, abandoned, which is a continuation of application No. 08/271,232, Jul. 6, 1994, abandoned, which is a continuation of application No. 07/897,873, Jun. 12, 1992, abandoned.

[51] Int. Cl.[7] .................................................... A61D 6/08
[52] U.S. Cl. ............................... 378/20; 378/63; 378/205
[58] Field of Search .................................... 378/162–164, 378/204, 205, 62, 63

[56] References Cited

U.S. PATENT DOCUMENTS

| | | | |
|---|---|---|---|
| 4,319,136 | 3/1982 | Jinkins | 378/163 |
| 4,341,220 | 7/1982 | Perry | 378/162 |
| 4,991,579 | 2/1991 | Allen | 128/653 |
| 5,052,035 | 9/1991 | Krupnick | 378/164 |

*Primary Examiner*—David P. Porta
*Attorney, Agent, or Firm*—Darby & Darby P.C.

[57] ABSTRACT

This invention relates to the quantitative determination of a target or volume in the living body relative to external apparatus based on CT (computer tomography) or other image data. The invention describes a means of taking CT image data of the anatomy and of natural or implanted index positions on the patient's body, and relating the CT data to a coordinate system related to external apparatus which may be in fixed position relative to the patient. One implementation uses a transformation between the CT image data coordinate system and the second coordinate system. This makes it possible to do frame-based or frameless stereotactic target identification and approaches without the need for attaching a frame to the patient at the time of CT scanning.

10 Claims, 3 Drawing Sheets

SYSTEM FOR DETERMINING TARGET POSITIONS IN THE BODY OBSERVED IN CT IMAGE DATA

This is a continuation of application Ser. No. 07/897,073 filed on Jun. 12, 1990, now abandoned, which is a continuation of application Ser. No. 08/271,232 filed on Jul. 6, 1994 now abandoned, which is a continuation of application Ser. No. 08/434,246 filed on May 3, 1995 now abandoned, which is a continuation of application Ser. No. 08/711,348 filed on Sep. 5, 1996 now abandoned.

BACKGROUND AND SUMMARY OF THE INVENTION

The use of CT (computer tomography) imaging methods in medicine is now widespread. It is also commonplace to attach frames or mechanical devices to the patient during CT scanning. A common application is in brain surgery where a head ring is attached to the patient's skull for the purpose of providing a reference platform at the time of CT image scanning. Typically, the head ring is fastened directly to the patient' skull by head posts and skull fixation means, such as sharpened, pointed screws on the head posts that anchor directly to the skull. This frame may then be used as a rigid platform onto which may be attached a localizer structure. When a patient is scanned with the localizer structure so rigidly attached to his skull, index marks from the localizer will appear on the scan slices and provide means for mathematically determining the coordinates of every image point seen in the CT slice relative to the head frame. This technique was described in detail in U.S. Pat. No. 4,608,977 by R. A. Brown, patent issued Sep. 2, 1986. This methodology has been commercialized successfully by Radionics, Inc. in the form of the BRW Brown-Roberts-Wells Stereotactic Instrument. The method has been successfully used for X-ray-based, CT, MRI, and P.E.T. scanning computer tomographic scanning.

A difficulty with this technique is that it requires placement of the head frame to the patient's head prior to CT scanning, and, in the surgical phase, the head ring must remain on the patient's head between the time of scanning and the time of surgery. This is satisfactory for surgery such as brain biopsy when the stereotactic biopsy surgery will be done within hours of the CT imaging. Typically it will involve putting the head frame on, attaching the localizer system to the head frame, performing the CT image scan to determine the index fiducial points of the localizer structure on the CT image planes, doing a calculation to relate mathematically the image data via the fiducial points to the coordinate frame of the head ring, and attaching a stereotactic arc system or guidance means to the head frame so as to achieve the calculated target with an instrument or probe, and thus, to do the biopsy. A similar methodology is practiced for so-called radiosurgery in which a similar procedure is carried out, except that the surgical probe is actually a beam of photons, and the guidance means is an accelerator which provides the source of photons. These photons are beamed to the target for treatment or destruction of the target volume by attaching the head ring directly to the accelerator and moving the head ring in space so that the target volume stands at the confluence of the photon beam paths.

It would be of significant advantage to be able to carry out the CT image data without having to place the head frame on the patient's head, rather than to have the head frame remain on the patient's head between the time of scanning and the time of surgery or radiosurgery. For instance, it may be wished to analyze the CT scanning data over an extended period so as to plan for a complex surgery or radiosurgery. It may also be desired to do repeat surgery or radiosurgery many times after image scanning, and extended over periods of days or weeks, making it inconvenient or impractical to leave the head ring attached to the patient's head for that period. Thus, it would be desirable to perform the CT image scanning at one time, and to be able to relate the image scanning data at any time in the future to a head frame or fixation means which may be applied to the patient at that later time of surgery or scanning. For example, a surgical head holder may be applied to the patient's head at the time of surgery after the patient has been anesthetized. It would be desirable to be able to relate the position of that head frame to the volumetric image data that has been acquired from the CT imaging procedure at a previous or at a subsequent time. Furthermore, it may be desirable not to attach the head frame to the patient at any time, but rather use so-called frameless stereotactic means, such as an operating arm, or other device, to access quantitatively volumes of targets in the patient's head based on the CT image data which has been stored and manipulated in a computer.

Thus, one specific implementation of the present invention relates to a method of achieving the above-state goal of being able to perform CT imaging without a head frame, accumulate that data in a computer, subsequently have the patient in the operating setting or radiosurgery or radiotherapy setting and, at that time, relate the CT image data to a coordinate reference frame in the operating theater or radiation suite, such as, for example, a head frame put on at the time of surgery. No head frame would need to be attached during the CT imaging or at the time of surgery necessarily, however, in one embodiment of the present system, a head holder may be applied at the time of surgery or radiation surgery, and the coordinate system related to that head holder is mathematically related to the coordinate system of the CT scanning machine by means of X-ray or optical imaging carried out at the time of surgery. In one embodiment, index markers may be placed on the patient's skin or attached to the patient's skull as an example of a means of defining a specific coordinate system related to the CT imaging itself. At the time of surgery, if a head frame is attached, X-ray images of the patient's head may be taken, and the index markers that have been attached to the patient's head may be visualized relative to index or fiducial points attached to the head frame. By analyzing the relative position of the patient-attached index points to the head frame-attached index points, a transformation can be made to relate the respective CT image coordinate frame to the coordinate frame of the head frame, the latter being the surgical or radiosurgical coordinate frame. Thus, in one embodiment, the present invention relates to a transformation from CT image coordinate frame to surgical coordinate frame at the time, or approximately the time, of surgery. The surgeon is thereby freed from the need to place a head frame onto the patient at the time of imaging, and subsequent surgical episodes can be done repeatedly with very precise reproducible means of mapping the CT image field onto the surgical field.

An alternate example of the present invention is to place the index marks on the patient's skin or to the patient's bone anatomy, such as the skull, using a frame or guidance means so as to put the markers in a specific, relative orientation. One example would be to put them on the principal axes of a Cartesian coordinate system relative to the skull. This could easily be done by an appropriately designed implantation guide device. The index marks then can be visualized during surgery at a subsequent time when another head frame is put on, or no frame is put on at all. The index marks may be visualized by external apparatus, such a linear accelerator collimator system or a fluoroscopic X-ray machine or some other surgical device. The position of the external apparatus may be thusly determined relative to the body. CT scanning can be done subsequently, and the CT data can be related to that Cartesian coordinate system. This is yet another embodiment of placing index markers in the head or the body so as to relate CT, X-ray, and other image modalities one to the other.

DESCRIPTION OF THE FIGURES

The drawings, which are part of this invention specification, show illustrative embodiment demonstrating the objectives and features of this invention, and are briefly described as follows.

DESCRIPTION OF ILLUSTRATIVE EMBODIMENTS OF THE INVENTION

A detailed illustration of several embodiments of the present invention is described in this specification. It is understood that other embodiments may be constructed with various forms, some which may differ from the illustrative embodiments described and disclosed herein. Thus, the present examples by way of figures and this specification are deemed to be desirable embodiments for the purposes of this patent disclosure and to provide examples on which the claims are based to define the scope of the invention, however, it is understood that they are merely representative and that other forms are possible, based on the present invention, by those skilled in the art.

Figure 1:
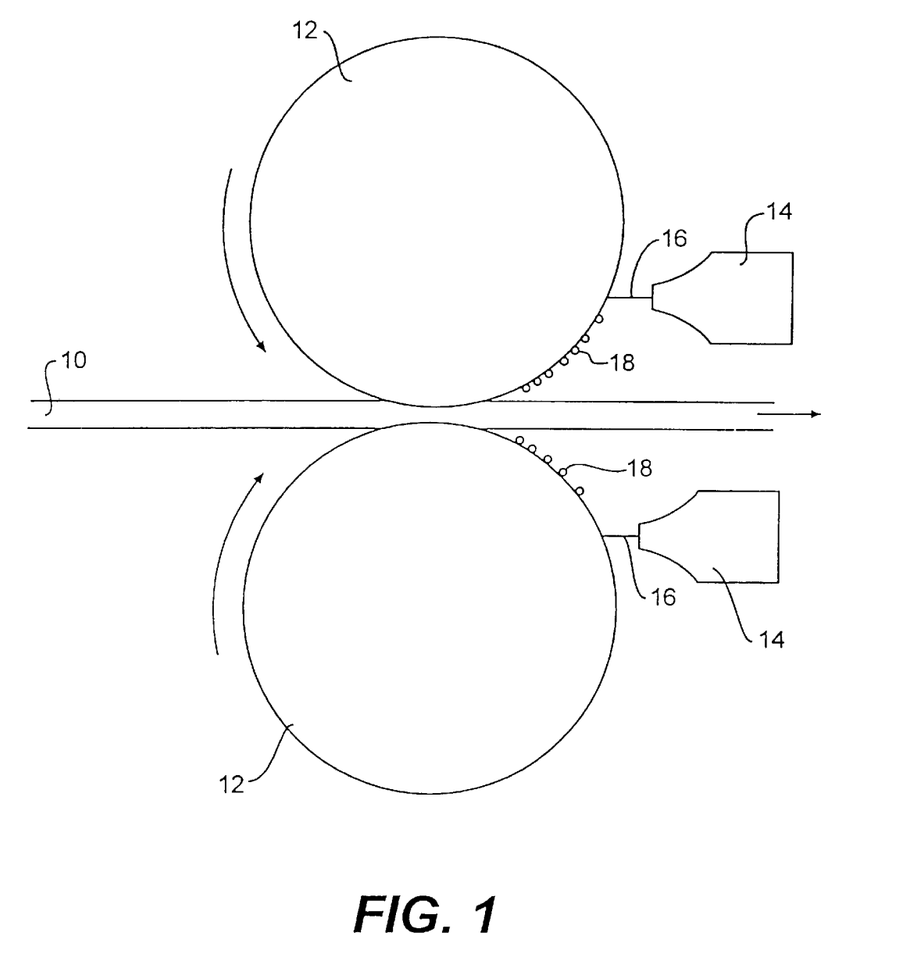
FIG. 1 is a schematic diagram of a CT system incorporating fiducial points on the patient's body in accordance with the present invention and illustrates the image scanner coordinate system.

Referring to FIG. 1, the patient 1 is being scanned by a CT scanner in this figure, which could be by X-rays, NMR (nuclear magnetic resonance), P.E.T. (proton emission tomography), or other computer tomographic modality. The stack of CT image planes 2 is meant to illustrate several of the many planes in which the image could be reconstructed. In this FIG. 1, the image planes are shown perpendicular to the Z axis, which characteristically is the axis of X-ray CT scanners; i.e. perpendicular to the X-ray source gantry. The slices are shown as Z1, Z2, . . . ZN, and represent a stack of reconstructed slices in the axial direction for this example. The slices could well have been stacked in the coronal or sagittal planes, which are perpendicular to these axial planes. A coordinate system represented by the axes X, Y, and Z in FIG. 1 would be the natural coordinate system of the CT scanner itself. The Z axis is perpendicular to the plane of the image slices, and the X and Y axes represent respectively the lateral axis and the anterior-posterior (A-P) axes relative to the CT scanning machine. In the typical X-ray CT scanner, the patient would be actually lying horizontally on a table which advances into the aperture of the scanner gantry. The Z axis, referred to as the axial direction, is roughly horizontal and perpendicular to the opening of the gantry aperture. It also runs roughly along the longitudinal axis of the patient's body. The X axis would actually be perpendicular to the Z axis, and runs roughly from the left to right orientation of the patient's body. The Y axis is an axis perpendicular to both the Z and X axes, and runs roughly anterior to posterior relative to the patient's body. There is an origin, OI, for the image scanner coordinate system represented in FIG. 1, which is defined by the scanner manufacture, and usually includes what would be defined as the zero slice for which the millimeter index for the slice reads zero on the CT scanner. Thus, each reconstructed planar slice defines the Z axis, or axial axis, relative to the scanning machine, and each two-dimensional image produced by such a CT scanning machine will have its own X and Y axes and be indexed by a Z coordinate value. These three axes are referred to as the scanner axes, and are represented by X, Y, Z in this specification and in FIG. 1. As illustrated further in FIG. 1, the CT image scanner comprises the physical machine 3, whether it be an X-ray, MRI, or P.E.T. scanning machine or other type of modality that determines these tomographic image slices. The data is processed by a processor 4 to produce slice displays illustrated by 5 in FIG. 1. These are usually brought up on a display console so that the operator may examine the anatomy and evaluate normal and pathological structures therein. The data from such a scanning machine may also be separately taken from the machine and put into a 3-D display processing computer illustrated by 6, which will then display in a three-dimensional format on a monitor 7 a representation of the patient's anatomy. Intrinsic to this data would be the machine-defined coordinates X, Y, Z, as illustrated in FIG. 1; that is, each point in each slice, and thus each point or voxel in the 3-D data set, would be tagged by its scanner coordinates X, Y, and Z. We have also shown in FIG. 1 index markers 10, 11, and 12, which have been attached to the patient's physical anatomy. These index markers can be of various types and forms. They may be radiopaque and/or MRI-visible structures that are stuck to the patient's skin. They may be radiopaque markers that are implanted in the patient's skull, a more permanent way of placing CT markers. They may alternatively be natural landmarks, such as the nasus, auditory meatus, the tip of the nose, or other fairly well defined points, lines, or surfaces on the patient's anatomy. They may alternatively be lines, strips, grids, structures with straight rods combined with diagonal rods, or other surface structures that could be attached to the patient's anatomy. These markers are also present in present or reconstructible in the display 7, and are illustrated here as 10A, 10B, and 10C.

An exemplary embodiment for the CT visible markers 10, 11, and 12 would be implanted screws or buttons that can be placed into holes in the patient's skull so that they will remain with the patient and are absolutely immovable relative to the skull. The numbers of these markers may vary depending on the analysis to be described below, but a number such as three or more is desirable. The markers for X-ray CT scanning could be made from stainless steel, tantalum, or other high Z material. For MRI scanning, they could be capsules with saline solution in them, for example, or they could have a slight magnetization so that on an MRI slice one could visualize a small void where the markers are. The markers could also be placed externally on the skin and could be relocated there by small skin tattoos. The markers could be such that they are visible in various type of CT scanners (viz., X-ray, MRI, PET, ultrasound, etc.) so that correlative or comparative image or registration analyses can be done. This is less well defined than skull-anchored markers since the skin can move, and, after long periods, it may be difficult to identify tattoos which may be near or under the hairline. The markers may further be linear structures or grids, however, point-like markers have an advantage of simplicity.

The purpose of the markers will be to relate the CT image scanner coordinate system to a second coordinate system relative to an attached head ring or patient fixation means attached to the body. Each of the markers is presumed to appear on a CT slice. As illustrated, the image point 15 in slice image 5 in FIG. 1 might represent one of the markers 10, 11, and 12 in the actual physical anatomy. By observing the positions of these image points on the individual 2-dimensional slice as well as the slice number in which they appear, one can relate the physical marker positions to the coordinate representation in the scanner coordinate system represented by the axes X, Y, and Z. Modern CT scanners in fact provide the user with an X and Y coordinate position (usually in millimeters) of each point (pixel) in the 2-dimensional display of a slice, and also readout digitally the slice position (usually in millimeters) corresponding to the position of the CT couch in the gantry, this latter position serving as the Z-coordinate. Thus for one on a multitude of slices (i.e. a scan volume), the X, Y, Z coordinates of the index marker and, indeed, all imaged points, is provided directly from the scanner. This data can be downloaded to other devices or computers by standard scanner outputs.

FIG. 1 also illustrates for completeness the transfer from the processing elements 3, 4, and 5 (which are usually built into modern CT scanners) to a 3-D display device 6 which can display the volume of CT slice data on display 7. The 3-D processing is not usually part of today's CT scanners, but is done by many companies as an ancillary visualization means.

Figure 2:
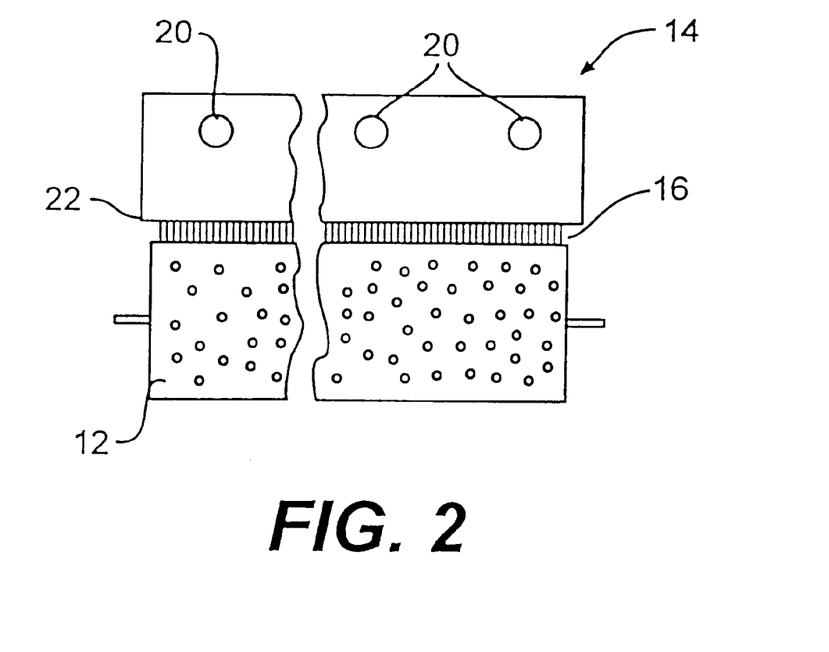
FIG. 2 illustrates a head frame or patient attachment means with its respective frame coordinate system.

Referring to FIG. 2, a second coordinate system, referred to as SF, may be defined relative to a head ring 220, and is indicated here as X', Y', Z' axes. The origin of the coordinate system is indicated by OF'. The head ring 220 is attached to the patient typically by head posts 221 and skull fixation screws 222. The head ring shown in FIG. 2 is similar to that for the BRW Stereotactic System referred to above. Alternatively, the patient attachment means could be an operating surgical head clamp, which is used for most neurosurgical procedures. An example of such a head clamp is the Mayfield Head Rest Clamp. It also is attached to the patient by means of three or more skull screws attached to a semi ring similar to that of 220 in FIG. 2. The markers 210, 211, and 212 are also shown in FIG. 2 still attached to the patient's head in the same position that they were during the CT scan as shown in FIG. 1. These markers have a known relationship to the image coordinate system SI in FIG. 1, but as yet their position relative to the frame coordinate system SF and its respective axes X', Y', and Z', is not known. If the orientation of the markers 210, 211, and 212 can be determined relative to the frame coordinate system SF, then the relationship of the data set, as displayed in the three-dimensional representation 7 in FIG. 1 can also be related quantitatively to the frame coordinate system.

Figure 3:
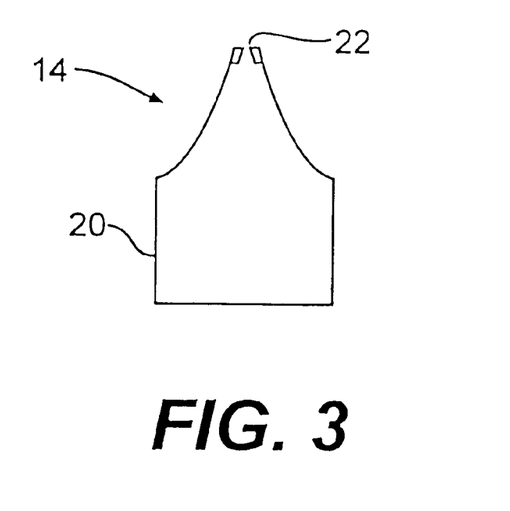
FIG. 3 illustrates an X-ray imaging method in accordance with the present invention system which is used to relate the scanner coordinate system to the head frame coordinate system by a transformation.

One embodiment of the present invention to make such a transformation between image coordinate system and frame coordinate system is illustrated in FIG. 3. Here two X-ray plane films are taken of the patient with the head ring 320 attached to his head (the head posts are not shown, but are assumed to be there in this picture). Shown in FIG. 3 are two X-ray film planes 330 and 331 and two corresponding sources of X-rays 323 and 324, respectively. The first source is a lateral X-ray source 323, and the other is an anterior-posterior (A-P) source 324. Attached to the head ring 320 are radiopaque square structures 325, 326, 327, and 328, which will appear on the X-ray films as squares, rectangles, or generally quadrilaterals, depending on the orientation of source 323 and film plane 330. Thus, for example, with source 323, which is located on the right side of the patient as it radiates through the patient's head, and the square structures 325 and 327, which are attached in a known position relative to head ring 320, the squares 325 and 327 will project as quadrilaterals 325A and 327A on the X-ray plane image 330. Similarly, for the A-P source of X-rays 324, the images of the squares 326 and 328 will appear as quadrilateral images 328A and 326A on the planar X-ray film plane 331. Also shown in FIG. 3 are the projected images of the markers 312, 310, and 311, as they appear on the X-ray planes 330 and 331. These are illustrated respectively as 310A, 311A, and 312A, and on the plane 330, and on the plane 331, they are 310B, 311B, and 312B. It is well known, and has been implemented for some years, that such lateral and frontal X-ray views with index squares, such as 325, 326, 327, and 328, projected on them will enable that the quantitative position of well identified objects, such as the markers 310, 311, and 312, when seen in both such planar X-ray images, can be mathematically determined relative to the head ring 320. This means that by quantitative analysis of the images on each plane 330 and 331 the actual coordinate values of each of the markers, i.e., the X', Y', Z' coordinates relative to the frame coordinates SF can be determined for each one of these markers. For a discussion of how this is done, the paper of Vandermeulen, et al. illustrates the technique, and the commercially sold product by Radionics, Inc., referred to as the SGV-AL Angiographic Localizer does precisely this operation. Therefore, from such a configuration and method as illustrated in FIG. 3, the frame coordinate values for the markers 310, 311, and 312 can be definitively determined with great accuracy. From such a calculation, the X', Y', and Z' coordinate values for each of the index markers 310, 311, and 312 can be calculated. The image processing of the data from FIG. 3 and these calculations might be done by the module 341 illustrated schematically in FIG. 3.

As has been described above, the X, Y, and Z coordinates for each of the index markers have also been determined in the scanner coordinate system. This means that each of the markers has been assigned a value X, Y, and Z by this means. The X and Y values from the image scanner are displayed on its two-dimensional readout, as shown in FIG. 1. The Z coordinate may be determined typically by knowing which slice number the index marker appears in. Typical CT scanners have metric readouts of the slice position with considerable accuracy, and thus the calibration in Z in the scanner coordinates may be determined directly from the relative position of the scanner couch and the scanner gantry with the appropriately built-in readout means. Thus, in fact, every visualized point of the image scanner can be assigned an X, Y, and Z coordinate value, not only the markers themselves. Thus, once the determination has been made of the linear transformation which maps each point X', Y', and Z' of the imaging coordinate system to each point X', Y', and Z' of the frame coordinate system, then the full correspondence between each point seen in the image scan data can be made relative to the frame coordinate system. Thus, the data from the imaging system can be transposed into data which corresponds to the frame coordinate system. That coordinate transformation can be made in several ways. One method illustrated here is that by knowing the individual coordinates of each of three independent markers, such as 310, 311, and 312, in FIG. 3 for the image coordinate system and the frame coordinate system, then the transformation matrix for these marker points can be determined, and thus the full transformation between any coordinates in the image coordinate system can be made to the frame coordinate system and vice versa.

A more specific illustration of the calculations discussed will now be given. To make the transformation alluded to in FIG. 3, the head ring 320 has affixed to it four plates, referred to as 325, 326, 327, and 328. Each of these plates has a square pattern on them, either as radiopaque lines or radiopaque dots indicating the corners. This is the geometry of the commercially available SGV-AL Angiographic Localizer from Radionics, Inc. When the lateral and the A-P X-ray is taken through the angiographic localizer and also the patient's head by means of the X-ray sources 323 and 324 respectively, the square patterns will show up as quadrilateral image patterns on the plane film X-ray views 331 and 330 respectively. These patterns are shown in FIG. 3 as the quadrilateral image lines 325A, 327A, 326A, and 328A. In addition, on each of the images is seen the patient's anatomy, as well as the images of the index markers 310, 311, and 312. These images of the image markers appear on the lateral X-ray image as 310A, 311A, and 312A, and on the A-P image as 310B, 311B, and 312B. Thus, each of the X-ray images has fiducial markings associated with the stereotactic apparatus, as well as fiducial markers representative of the position of the patient's anatomy. As mentioned above, the fiducial markers relative to the patient's anatomy are known in the scanner coordinate system since they appear on the scan images, and are thus referenced relative to the scan coordinate system. The object of the instrumentation in FIG. 3 is to determine the coordinates of the reference markers in the stereotactic coordinate system X', Y', and Z' as shown in FIG. 2. This can be done by a method of projective geometry, which has been described in the paper of Vandermeulen, et al., referred to above. The process for making such calculations in frame coordinates is handled by the image acquisition elements 340 in FIG. 3, which involve either digitization of the entire X-ray images or will involve point-by-point pickoff of the coordinates of all of the structures in each of the lateral and A-P images. Information from the data acquisition is then fed into a data processing and stereotactic frame coordinate calculation instrumentation indicated by 341 in FIG. 3. From this the X', Y', and Z' coordinates for each of the index markers 310, 311, and 312 relative to the stereotactic frame can be calculated uniquely.

At this point, the coordinates for the three markers are known in both the image coordinate system and the frame coordinate system, and a linear transformation F can be carried out to relate thereby any point in the image coordinate system SI to their associated position or coordinates in the frame coordinate system SF. [F] is a 3×3 matrix with coefficients $F_{nm}$. Let the 3 markers be designated as A, B, and C. For A, its coordinates in SF are $A'_n$, where n=x', y', or z'; and its coordinates in SI are $A_m$, where m=x, y, or z indices. Then $A'_n = F_{nx}A_x + F_{ny}A_y + F_{nz}A_z$, for n=x', y', and z'. Similar equations hold for $B'_n$ and $C'_n$. From these 9 equations, the coefficients of Fnm can be determined, since all the coordinates of A, B, and C are known. Hence, for any other point D in the space, $$D' = [F]D$$

i.e. the transformation from SI to SF is known. These matrix methods are standard in linear algebra. In addition, one can add to these translations a linear offset or translation term to take account of different origins of the transformed coordinate systems.

Once such a transformation has been made, then some or all of the image data of the patient's anatomy, as seen on the CT scanner, can be transformed into frame coordinates and can be represented in three-dimensional space for visualization and analysis, as represented by the process of 343 and the image display means 344 in FIG. 3.

It is understood that variations in the specific nature, form, and process of the embodiments shown in FIG. 1, 2, and 3 are possible. Such variations where they do not depart from the overall concept of the present invention we will claim accordingly in the claims of this patent application below. Examples of such variations would be different confirmations of head rings, as shown in FIG. 2, variations in the concept of index markers. For example, instead of point or point-like index markers, the index markers could be lines, grids, volumes, or have distinguishing shapes or signature so that they can be identified one from the other. Markers can be made out of a variety of materials, including metals, composites, radiopaque or MRI illuminating filled media, vessels that can contain fluid for MRI visibility or P.E.T. scanning, screws that can be anchored to the skull, patches that can be stuck to the skin, wires that can be laid on the surface of the anatomy or embedded under the skin, and other such variations. The angiographic or X-ray squares, as shown in FIG. 3, can also be varied in other geometries or configurations so as to index the planar views 330 and 331 to make the coordinate transformation. Natural anatomical landmarks can also be used for this purpose rather than index markers placed in the anatomy itself. For example, the point of the nose, the nasium, the points or positions of the ears, etc. could be used. Tattoo marks could be placed on the skin, and the markers could be placed on and taken away at the time or after imaging or surgery. To achieve the images in FIG. 3, simple two-directional X-ray machines may be used, or fluoroscopy may be used. Such machines are readily available in operating rooms, so this can be done at the time of surgery. In the case of radiosurgery or radiotherapy, such X-ray shots can be taken as the patient is placed on the radiation machine, and thus the transformation from image coordinates to frame coordinates can be done immediately or used as a verification check. Different types of secondary imaging modalities may be used such as ultrasonic rather than X-rays.

In the situation of surgery, very frequently a head holder or head clamp in attached to the patient's head, or other anatomy, after he is anesthetized. Then a sterile draping is placed over the head and the head clamp or head ring in preparation for surgery. During surgery, a stereotactic arc or an operating arm may be used to identify anatomical points in the surgical field, and these points should be referenced to the CT scanner information. The head ring may have adaption means so that the angiographic or X-ray plates, such as in FIG. 3, can be attached to the ring through the sterile drape at the time for surgery, and the coordinate transformation confirmed or calculated during surgery to assure that the surgeon has the proper orientation of the anatomy read relative to the head ring. Thus, subsequently, when a stereotactic arc or an operating arm is attached to or related to the position of the head ring 320 in FIG. 3, the corresponding associated relationships to the patient's anatomy will also be known. This is assured by taking such X-ray films as shown in FIG. 3 and doing the transformation and thus coordinate system mapping, as described above. In the field of "frameless stereotaxy" where a scan is done without a head holder on the patient's head, and later in a surgical setting the head clamp or head ring is placed on after anesthesia, such a check or coordinate transformation at the site of surgery is very important. Use of discrete index markers, such as small screws implanted in the skull, give a level of assurance in this operation. Such screws would not move and would be carried with the patient indefinitely. Thus, in a situation of repeat surgery or when the surgery is separated widely from the time of CT scanning, one is assured that the index marks have not moved, and thus their transformation, as illustrated in FIG. 3, will provide a faithful mapping from CT image coordinates to the apparatus associated with the surgery or radiation therapy.

Other forms of index imaging, such as illustrated in FIG. 3, may also be devised. Instead of two planar X-ray films, a CT or MRI scan may be performed after the initial scan, and the positions of the index markers seen again on another of these tomographic type processes. By so doing, again the position of the index markers can be transferred from one coordinate system to another. Accordingly, FIG. 3 is meant only as an one example of the secondary imaging process in which the index markers are seen again and their position calculated relative to the secondary imaging process apparatus, and thus the transformation made to the original CT scanning image in which the markers are seen first.

Figure 4:
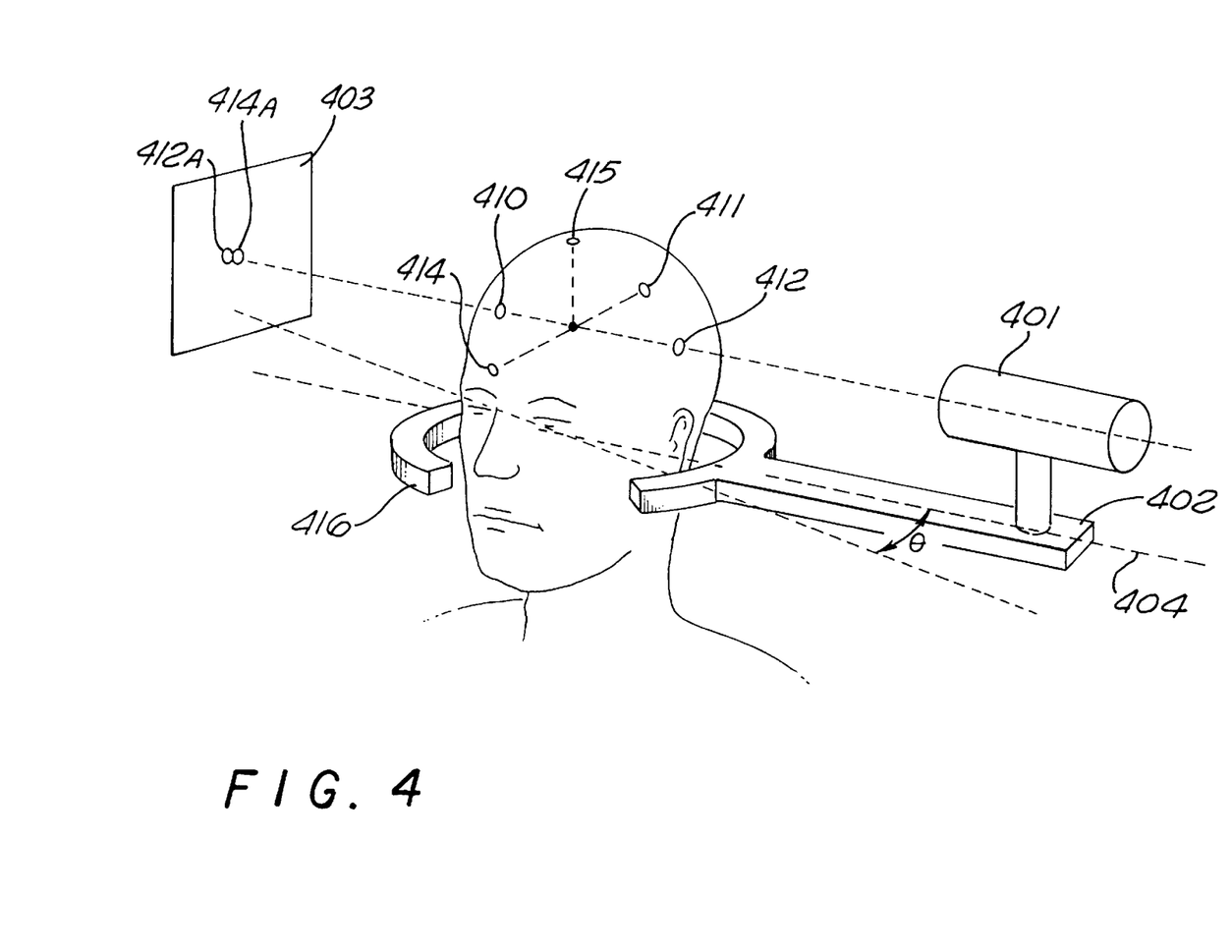
FIG. 4 illustrates the registration of an external apparatus to the patient's head by means of pre-placed index marks.

In addition to the examples given above, other implementations of the present invention can be thought of. One such implementation is illustrated in FIG. 4. There the index marks 410, 411, 412, and 414 are placed on an orthogonal coordinate system or a Cartesian coordinate system in the patient's head. Another index spot, 415, might be put on the node or zenith of such a coordinate system. This can be implemented by a special guidance apparatus that could be devised so as to insert the index marks on such a coordinate or Cartesian axis. It is not necessary that all index marks are on such a Cartesian axis, but this could be convenient in some situations. Subsequently, a head ring, as illustrated by 416, may or may not be placed on the patient's head. If such a ring is placed on the patient's head, then external apparatus indicated schematically by the arm 402 may be known as orientation relative to the head ring 416. If one wishes to know the orientation of the apparatus 402, which is simply diagramized as a bar in this case, but could be a much more complicated stereotactic or guidance means, then one could use an X-ray tube or X-ray beam in a guidance device such as 401 to orient the apparatus along the line between index points 410 and 412. This could be determined by means of the X-ray screen 403 and the associated dots 414A and 412A, which will be images of the index marks 412 and 414 respectively on the screen. Thus, by orienting the X-ray source and thus the guidance apparatus 401 and 402 so that the image spots are coincident on the screen 403, one automatically lines up the external apparatus 402 relative to that axis in the patient's body. Similar steps could be taken to align an apparatus along the lines of index points 411 and 414. In this way, one can establish with external apparatus the same coordinate system that was determined previously by the implantation of the index marks.

Subsequent CT imaging could then visualize these marks or dots and their reference to the entire anatomy as seen on the CT or MRI image data. The CT image data coordinate frame can be related to the index mark frame via a transformation or a simple stacking of data which is in planes parallel to the principal axes of the Cartesian coordinate system represented by the index marks. Thus one has the ability with such index dots to alternate between image modalities and thus transform or replicate orientations from one episode to the next.

One can also align the X-ray source or fluoroscopic C-Arm 401 so that it merely picks up the images of 410 and 412 on a screen 403. The relative orientation of those images could determine the position of the X-ray tube 401 relative to the anatomy. In other words, a coincidence of the images 412A and 414A is not necessary to establish the orientation. This is similar to, what was illustrated in FIG. 3 previously. Index reticules or bomb sites could be attached to the head ring 416 so as to put further reference lines or marks on the screen 403 with the index images 412A and 414A so as to produce further reference information.

It is to be recognized that this technique can be used throughout the body, and the example in the anatomy of the head is used only as illustration. It is also recognized that it can be used in conjunction with a variety of other processes, methods, or surgery involving stereotactic arcs, operating arms, robotic devices, and invasive or non-invasive probe or diagnostic means. Various forms of the CT scanner, display devices, and data processing components may also be envisaged, and it is intended that this invention claims such variations of method. Now, having described the invention, the scope shall be defined generally by the claim set forth below:

We claim:

1. A method for identifying an orientation of an apparatus used in the treatment of a patient's anatomy as determined from computer tomographic (CT) image data, said method comprising the steps of:

(a) attaching CT detectable markers onto a patient's anatomy to form coordinate markers in the CT imaging data which identify the position of the markers relative to the patient's anatomy;

(b) generating CT imaging data of the patient's anatomy, said CT imaging data containing data identifying the position of the CT detectable markers relative to the patient's anatomy;

(c) taking images of the patient from at least one direction with an imaging means, said imaging means being positioned relative to said apparatus, for detecting said detectable markers whereby the orientation of said patient's anatomy as visualized in said CT image data relative to said apparatus is determined relative to said imaging means.

2. A system for identifying an orientation of an apparatus used in the treatment of a patient's anatomy with the patient's anatomy being visualized from CT scanner image data, said system comprising:

(a) CT image detectable markers that are attachable to said patient's anatomy and which are visualized and thus related spatially in said CT scanner image data relative to said patient's anatomy;

(b) an apparatus having X-ray visible reference structures, said apparatus being positioned relative to the patient's anatomy so that both the X-ray visible reference structures of the apparatus and the CT image detectable markers are visible under X-ray imaging whereby the position of said apparatus is determined relative to said patient's anatomy.

3. An apparatus for relating the CT scanner image data of a patient's anatomy obtained from a CT scanner to that of image data from an imaging device, said apparatus comprising:

(a) index means for placement on the patient's anatomy, said index means being detectable in said CT scanner image data and also in said imaging device data whereby the position of said index means relative to said patient's anatomy is determined from said CT scanner image data and said imaging device data;

(b) a support structure positioned relative to said patient's anatomy and to said imaging device so that image data from said imaging device of both said patient's anatomy and of said index means can be used to determine the position of said support structure with respect to said patient's anatomy as the anatomy is visualized by said CT scanner image data.

4. The apparatus of claim 3 wherein said support structure is a rigid structure with radiopaque indices attached thereto, and wherein said image device is an X-ray machine.

5. The apparatus of claim 4 wherein said radiopacue indices are radiopaque point-like structures located in known positions relative to said support structure.

6. The apparatus of claim 5 wherein said patient's anatomy has bony structures and wherein said radiopaque indices are radiopaque marks that are attached in a fixed position relative to the bony structures of said patient's anatomy.

7. The apparatus of claim 3 wherein said index means comprises radiopaque indices.

8. The method of claim 1 wherein said imaging means is a computer tomographic imager.

9. The method of claim 1 wherein said imaging means is an X-ray imager.

10. The method of claim 1 wherein said imaging means is a magnetic resonance imager.

* * * * *

UNITED STATES PATENT AND TRADEMARK OFFICE
CERTIFICATE OF CORRECTION

PATENT NO. : 6,122,341
DATED : September 9, 2000
INVENTOR(S) : William Butler et al.

It is certified that error appears in the above-identified patent and that said Letters Patent is hereby corrected as shown below:

Title page shyould be deleted and replace witht the tilte page as shown on the attached page.

Delete Figures 1-3, and substitute therefore the Figures, 1-3 as shown on the attached page.

Signed and Sealed this

Eighth Day of January, 2002

Attest:

JAMES E. ROGAN
*Director of the United States Patent and Trademark Office*

*Attesting Officer*

United States Patent [19]
Butler et al.

[11] Patent Number: 6,122,341
[45] Date of Patent: Sep. 19, 2000

[54] SYSTEM FOR DETERMINING TARGET POSITIONS IN THE BODY OBSERVED IN CT IMAGE DATA

[76] Inventors: William E. Butler, No. 4- 134 Prince St., Boston, Mass. 02113; Paul H. Chapman, 97 Chestnut St., North Reading, Mass. 01864; Eric R. Cosman, 872 Concord Ave., Belmont, Mass. 02178

[21] Appl. No.: 08/969,078

[22] Filed: Nov. 12, 1997

Related U.S. Application Data

[63] Continuation of application No. 08/711,348, Sep. 5, 1996, abandoned, which is a continuation of application No. 08/434,246, May 3, 1995, abandoned, which is a continuation of application No. 08/271,232, Jul. 6, 1994, abandoned, which is a continuation of application No. 07/897,873, Jun. 12, 1992, abandoned.

[51] Int. Cl.[7] ............................................. A61D 6/08
[52] U.S. Cl. ........................... 378/20; 378/63; 378/205
[58] Field of Search ............................... 378/162–164, 378/204, 205, 62, 63

[56] References Cited

U.S. PATENT DOCUMENTS

| | | | |
|---|---|---|---|
| 4,319,136 | 3/1982 | Jinkins | 378/163 |
| 4,341,220 | 7/1982 | Perry | 378/162 |
| 4,991,579 | 2/1991 | Allen | 128/653 |
| 5,052,035 | 9/1991 | Krupnick | 378/164 |

*Primary Examiner*—David P. Porta
*Attorney, Agent, or Firm*—Darby & Darby P.C.

[57] ABSTRACT

This invention relates to the quantitative determination of a target or volume in the living body relative to external apparatus based on CT (computer tomography) or other image data. The invention describes a means of taking CT image data of the anatomy and of natural or implanted index positions on the patient's body, and relating the CT data to a coordinate system related to external apparatus which may be in fixed position relative to the patient. One implementation uses a transformation between the CT image data coordinate system and the second coordinate system. This makes it possible to do frame-based or frameless stereotactic target identification and approaches without the need for attaching a frame to the patient at the time of CT scanning.

10 Claims, 3 Drawing Sheets